United States Patent [19]

Hoshino

[11] Patent Number: 4,832,979
[45] Date of Patent: May 23, 1989

[54] PROCESS FOR PREPARING LASER KNIFE

[76] Inventor: Masahiko Hoshino, Corpo Yanagisawa 202, No. 3-14, Kizawaminami 2-chome, Toda-shi, Saitama, Japan

[21] Appl. No.: 95,454

[22] Filed: Sep. 11, 1987

[30] Foreign Application Priority Data

Nov. 21, 1986 [JP] Japan .................. 61-278264

[51] Int. Cl.$^4$ .............. C23C 14/00; A61B 17/36; B05D 3/06
[52] U.S. Cl. .................. 427/38; 128/303.1; 204/192.16; 204/192.22; 204/192.23; 204/192.31
[58] Field of Search .......... 128/303.1, 395, 396, 128/397, 398; 204/192.31, 192.16, 192.22, 192.23, 192.28; 427/38; 604/20, 21, 22; 219/121 L, 121 LG, 121 LV

[56] References Cited

U.S. PATENT DOCUMENTS 4,736,743 4/1988 Daikuzono .................. 128/303.1

FOREIGN PATENT DOCUMENTS 138678 11/1979 German Democratic Rep.
133716 5/1977 Japan.

OTHER PUBLICATIONS

Vossen et al., *Thim Film Processes*, (Academic Press, New York), ©1978, pp. 131-134, 167-170.
Bunshah et al., *Deposition Technologies for Films and Coatings*, ©1983 (Noyes, Park Ridge), pp. 244-245.

*Primary Examiner*—Norman Morgenstern
*Assistant Examiner*—Margaret Bueker
*Attorney, Agent, or Firm*—James E. Nilles; Donald C. McGaughey

[57] ABSTRACT

A process for preparing a laser knife wherein on the surface of a probe portion of a laser knife are coated with a carbon coating of 1 μm to 50 μm in thickness and a protective coating of 1 μm to 50 μm in thickness in that order by either a sputtering method or an ion plating method. The protective coating is made of sapphire, ruby or quartz glass.

3 Claims, 1 Drawing Sheet

PROCESS FOR PREPARING LASER KNIFE

BACKGROUND OF THE INVENTION

1. Field of the Invention

This invention relates to a process for preparing a medical laser knife equipped with a probe portion which generates heat.

2. Description of the Prior Art

A laser knife which has been commonly used is operated as follows. A laser beam emitted from a light source is led through an optical fiber to a probe portion made of, e.g., sapphire ($\alpha$-$Al_2O_3$) or quartz glass ($SiO_2$) provided at the tip of the knife. Various operations such as amputation, incision, or hemostasis through coagulation are performed by light beam radiation from the probe portion with or without pressing the probe portion against the affected part or the part to be operated.

However, such a laser knife is poor in efficiency with respect to e.g., amputation or resection, because a laser beam energy is transferred to the cells, where it is absorbed and converted into a heat energy.

In my work on the invention disclosed herein I considered a possible method of improving the efficiency of the laser probe by providing a carbon coating which can convert a part of the laser beam energy into a heat energy on the surface of the probe portion of the laser knife to take incising or amputating the affected part or the part to advantage of a combination of the laser beam energy with the heat energy when incising or amputating the part to be operated on.

I applied amorphous carbon powder on the surface of the probe portion together with a binder to form the carbon coating, and then applied sapphire ($\alpha$-$Al_2O_3$) or quartz glass ($SiO_2$) in a molten state applied on the surface of the carbon coating to form a protective coating for the purpose of preventing the combustion of the carbon powder.

However, the formation of my carbon coating and the protective coating by the above-mentioned method has disadvantages such as poor durability of the laser knife because of frequent occurrence of peeling of the coating attributable to poor adhesion between the probe portion and the carbon coating. Further, in this method, it is difficult to form a coating having a uniform thickness, which tends to cause uneven generation of heat.

SUMMARY OF THE INVENTION

The present invention has been made in order to solve the above-mentioned problems. Specifically, an object of the present invention is to provide a process for preparing a laser knife which has excellent durability and can stably generate the heat.

In accordance with the present invention, there is provided a process for preparing a laser knife comprising successively coating the surface of a probe portion of a laser knife with a carbon coating and a protective coating in that order by either a sputtering method or an ion plating method.

In the present invention, the probe portion of a laser knife is first coated with carbon by either a sputtering method or an ion plating method. Thereafter, the carbon coating thus formed is coated with a protective material by either a sputtering method or an ion plating method.

The foregoing and other objects and features of the present invention will be apparent from the following description taken in connection with the accompanying drawings.

DESCRIPTION OF THE PREFERRED EMBODIMENT

Figure 1:
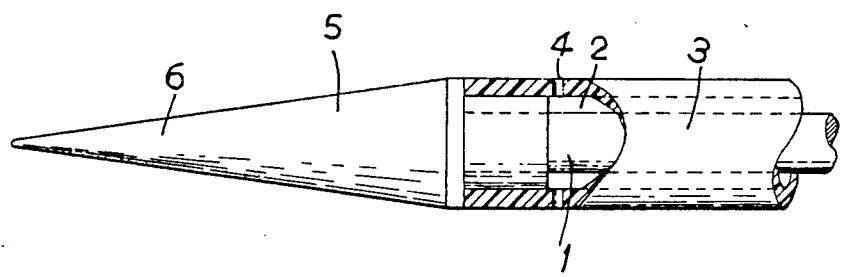
FIG. 1 is a partially cutaway side view of a laser knife illustrating one example of the present invention.

In FIG. 1, numeral 1 designates a fiber light guide having a circular shape in its crosssection. The fiber light guide 1 is comprised of, e.g., quartz glass ($SiO_2$) and is connected to a laser beam source not shown in the drawing. An external tube 3 is provided in a coaxial form on the outer periphery of the fiber light guide 1 through the medium of a gap 2 constituting a water passage. An outlet pore 4 is provided near the terminal of the external tube 3 by perforation.

Figure 2:
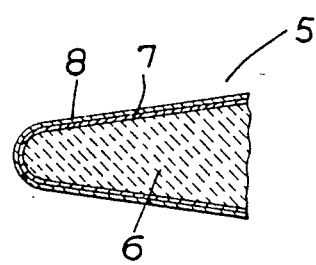
FIG. 2 is a partial crosssectional view of the laser knife as shown in FIG. 1.

Numeral 5 is a probe portion made of sapphire, ruby or the like ($\alpha$-$Al_2O_3$), or quartz glass ($SiO_2$) and having, e.g., a conical shape. As shown in FIG. 2, the probe portion 5 has a tip 6 the surface of which is coated with a carbon coating 7 of from 1 $\mu$m to 50 $\mu$m in thickness. On the carbon coating 7 is provided a protective coating 8 made of sapphire, ruby or the like ($\alpha$-$Al_2O_3$) or quartz glass ($SiO_2$) and of from 1 $\mu$m to 50 $\mu$m in thickness. Therefore, the total thickness of these coatings is from 2 $\mu$m to 100 $\mu$m.

The carbon coating 7 and protective coating 8 are formed as follows. First, a nickel or iron mask is arranged at the boundary between the tip 6 of the probe portion 5 where the formation of the carbon coating 7 is required and a portion where no formation of the carbon coating 7 is required, thereby shielding the portion where no formation of the carbon coating 7 is required.

The probe portion 5 is heated at 300° C. or above. At the same time, a cathode voltage is applied to the probe portion 5. The carbon coating 7 is formed by a sputtering method as follows. A strong electric field is formed using, e.g., a magnetron to produce a magnetic field, and argon in the atmosphere is collided in the form of a cation against a carbon piece as the target. This evaporates carbon atoms present on the surface of the carbon piece. The carbon atoms are absorbed on the probe portion 5 of the cathode and are deposited on the surface of the probe portion 5 while heating the probe portion 5 until the coating is formed in a desired thickness. After formation of the carbon coating 7 in a desired thickness, a protective material comprised of sapphire, ruby or the like ($\alpha$-$Al_2O_3$) or quartz glass ($SiO_2$) is deposited on the surface of the carbon coating 7 by the same method, i.e., by sputtering, to attain a desired thickness, thereby forming a protective coating 8.

With respect to the method of forming the coating, an ion plating method can be used besides the above-mentioned sputtering method. The ion plating method comprises heating the probe portion 5, evaporating the material to be deposited using the probe portion 5 as the cathode, passing the evaporated material through a plasma to cationize the same, and accelerating the cationized material in an electric field, thereby absorbing the cationized material on the probe portion 5 as the cathode. That is, in the ion plating method, the material to be deposited is absorbed on the probe portion 5 by imparting such properties as will cause mutual attraction between the material to be deposited and the probe portion 5.

When using the laser knife thus prepared, a laser beam having a wavelength of, e.g., 1060 nm is fed from a laser beam source not shown in the drawing through the fiber light guide 1 into the probe portion 5. The affected part or the part to be operated is exposed not only to a laser beam energy emitted from the tip 6 of the probe portion 5 but also to a heat energy which has been converted from part of the laser beam energy by means of the carbon coating 7 on the tip 6, thereby incising or amputating the affected part or the part to be operated. At this time, in order to cool the tip 6 of the probe portion 5 or to wash off blood etc., a liquid such as water or a medicine is flowed through the gap 2 and is discharged through the outlet pore 4.

The carbon coating 7 and the protective coating 8 need not necessarily be formed by the same method. Specifically, one of the two coatings may be formed by the sputtering method while the other coating may be formed by the ion plating method.

According to the above-mentioned example, the formation of the carbon coating 7 and the protective coating 8 by either the sputtering method or ion plating method not only enables uniform generation of heat by virtue of a uniform coating thickness but also improves the durability of the laser knife by virtue of excellent adhesion of the carbon coating 7 and the protective coating 8. Further, the provision of the carbon coating 7 enables a simultaneous radiation of a laser beam energy and a heat energy from the probe portion 5, which contributes to an improvement in the efficiency of amputation, incision, and hemostasis through coagulation in the part to be operated or the affected part.

Moreover, the provision of the protective coating 8 on the carbon coating 7 prevents the combustion of carbon due to a laser beam energy. Still further, since the carbon coating 7 is formed only on the tip 6, no heat is generated in the holding portion, which renders the laser knife convenient for use.

According to the present invention, the carbon coating and the protective coating are formed by either the sputtering method or ion plating method, which enables uniform generation of heat by virtue of a uniform coating thickness and improves the durability of the laser knife by virtue of excellent adhesion of the carbon coating 7 and the protective coating 8, thus leading to an improvement in the efficiency on the use of the laser knife.

What is claimed is:

1. A process for preparing a laser knife comprising successively coating the surface of a probe portion of a laser knife with a carbon coating and a protective coating in that order by either a sputtering method or an ion plating method.

2. The process for preparing a laser knife according to claim 1, wherein said carbon coating and protective coating are of from 1 $\mu$m to 50 $\mu$m in thickness, respectively.

3. The process for preparing a laser knife according to claim 1, wherein said protective coating is made of sapphire, ruby or quartz glass.

* * * * *